United States Patent [19]
Malen et al.

[11] 3,989,834
[45] Nov. 2, 1976

[54] ALKOXY ANILIDES AND PHARMACEUTICAL COMPOSITIONS

[75] Inventors: Charles Malen, Fresnes; Pierre Roger, St-Cloud; Jean-Claude Poignant, Bures, Yvette; Xavier Pascaud, Paris, all of France

[73] Assignee: Science Union et Cie, Societe Francaise de Recherche Medical, Suresnes, France

[22] Filed: Mar. 13, 1975

[21] Appl. No.: 558,043

[30] Foreign Application Priority Data

Mar. 18, 1974 United Kingdom............... 11868/74

[52] U.S. Cl............................. 424/267; 260/293.77; 260/326.85; 260/559 A; 424/274; 424/324
[51] Int. Cl.².............. A61K 31/445; C07D 211/06
[58] Field of Search................. 260/293.77; 424/267

[56] References Cited
UNITED STATES PATENTS

| | | |
|---|---|---|
| 2,885,403 | 5/1959 | Beaver et al.................. 260/293.77 |
| 2,921,077 | 1/1960 | Hiltmann et al.............. 260/293.77 |
| 2,955,111 | 10/1960 | Ekenstom et al............. 260/293.77 |
| 3,124,586 | 3/1964 | Zenitz................................ 424/267 |
| 3,154,557 | 10/1964 | Zenitz............................ 260/293.77 |
| 3,192,213 | 6/1965 | Krapcho ........................ 260/293.77 |
| 3,192,214 | 6/1965 | Krapcho ........................ 260/293.77 |
| 3,213,099 | 10/1965 | Ekenstom et al............. 260/293.77 |
| 3,729,470 | 4/1973 | Vaille............................. 260/293.77 |
| 3,758,481 | 9/1973 | Hya................................ 260/293.77 |
| 3,839,570 | 10/1974 | Baile et al........................... 424/267 |

*Primary Examiner*—Donald B. Moyer
*Attorney, Agent, or Firm*—Behr & Woodbridge

[57] ABSTRACT

This invention relates to ortho-alkoxy anilines having the amino group substituted with an amino lower alkyl carboxylic residue, as well as their physiologically-compatible acid-addition salts and their optically-active isomers.

7 Claims, No Drawings

ALKOXY ANILIDES AND PHARMACEUTICAL COMPOSITIONS

This invention also relates to processes for making the same in which an ortho-alkoxy aniline is reacted with a lower alkanoic acid or a functional derivative thereof.

The compounds of the invention have therapeutical utility namely for the prevention or treatment of digestive disorders and gastric ulcers.

DESCRIPTION OF THE PRIOR ART

The prior art may be illustrated with the french patent 2.092.039 (to Bristol-Myers) which relates α-amino isopropionylanilides.

SUMMARY OF THE INVENTION

This invention relates to o alkoxy anilides substituted on the amino group with an amino lower alkyl carboxylic residue having the formula

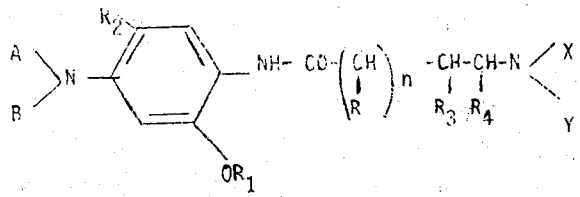

in which
   $n$ is zero or an integer from one to three,
   R represents a hydrogen atom or a lower alkyl radical,
   $R_1$ represents a lower alkyl radical, a lower alkenyl radical or a phenyl-lower alkyl radical,
   $R_2$ represents a lower alkoxy radical a halogen atom, a cyano radical, a lower alkylthio radical or a trifluoromethoxy radical,
   $R_3$ represents a hydrogen atom or a lower alkyl radical,
   $R_4$ represents a hydrogen atom or a lower alkyl radical,
   X and Y, which may be the same or different, each represents a lower alkyl radical or X and Y together form an alkylene chain optionally interrupted with one or two other heteroatoms and having from 3 to 7 ring members, or X and $R_3$ together form an alkylene chain having from 2 to 4 carbon atoms or X and $R_4$ together form an alkylene chain having from 2 to 4 carbon atoms optionally containing one or two hetero-atoms.
   A and B, which may be the same or different, each represents a hydrogen atom, a lower alkyl radical or an acyl radical derived from an organic carboxylic acid having from 1 to 18 carbon atoms, or A and B are both oxygen atoms or A and B together form an alkylene chain having from 2 to 6 carbon atoms.

The invention also provides the salts thereof, preferably by adding a therapeutically compatible mineral or organic acid.

When the amino alkyl carboxylic side chain contains at least one saymetric carbon, the compounds may be resolved into their optically-active isomers.

These compounds may be produced by acylating an ortho-substituted aniline with a lower alkyl carboxylic acid bearing at the end of the carbon chain an amino group or a substituent which may be easily split.

This invention relates to the pharmaceutical compositions incorporating as active ingredient at least one compound of the formula 1 or a salt thereof with an inert non-toxic pharmaceutical carrier.

This invention also relates to a method for treating or preventing gastric ulcers due to gastric hypersecretion or delay in gastric evacuation which consists in administering to warm-blooded animals suffering from said ailments a small but efficient amount of a compound of the formula 1 or a salt thereof, or to warm-blooded animals disposed to suffer from said ailments a small but efficient amount of a compound of the formula 1 or a salt thereof.

PREFERRED EMBODIMENTS

This invention relates to ortho-alkoxy-anilides, to a process for their preparation and to pharmaceutical compositions containing them.

The present invention provides ortho-alkoxy-anilides of the general formula

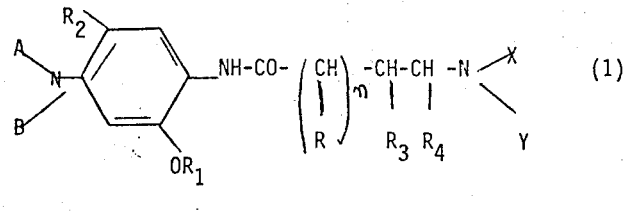

in which
   $n$ is zero or an integer from one to three,
   R represents a hydrogen atom or a lower alkyl radical,
   $R_1$ represents a lower alkyl radical, a lower alkenyl radical or a phenyl-lower alkyl radical,
   $R_2$ represents a lower alkoxy radical a halogen atom, a cyano radical, a lower alkylthio radical or a trifluoromethoxy radical.
   $R_3$ represents a hydrogen atom or a lower alkyl radical,
   $R_4$ represents a hydrogen atom or a lower alkyl radical,
   X and Y, which may be the same or different, each represents a lower alkyl radical or X and Y together form an alkylene chain optionally interrupted with one or two other hetero-atoms and having from 3 to 7 ring members, or X and $R_3$ together form an alkylene chain having from 2 to 4 carbon atoms or X and $R_4$ together form an alkylene chain having from 2 to 4 carbon atoms optionally containing one or two hetero-atoms,
   A and B, which may be the same or different, each represents a hydrogen atom, a lower alkyl radical or an acyl radical derived from an organic carboxylic acid having from 1 to 18 carbon atoms, or A and B are both oxygen atoms or A and B together form an alkylene chain having from 2 to 6 carbon atoms.

The present invention also provides salts of the compounds of the general formula 1 with physiologically compatible inorgenic an organic acids.

The term "lower alkyl" is used above to denote a linear or branched saturated hydrocarbon chain having from 1 to 6 carbon atoms, for example, a methyl, an ethyl, an isopropyl or a tertiary butyl radical.

The term "lower alkenyl" is used above to denote a hydrocarbon chain containing a carbon-carbon double bond, and having from 2 to 6 carbon atoms, for example an allyl or a pentenyl radical.

The term phenyl-lower alkyl designates a phenyl — or a substituted phenyl bearing a hydrocarbyl residue having from 1 to 4 carbon atoms. The hydrocarbyl residue may be straight or branched chain. The phenyl ring may carry substituent or substituents such as methoxy, trifluoromethyl, halogen, lower alkyl, lower alkylthio and lower acylamino. Examples of such phenyl (lower alkyl) radicals are 3, 4- dimethoxy benzyl, benzyl, m-trifluoromethyl benzyl, α-methyl benzyl, p-chlorobenzyl, phenylethyl, phenyl propyl, β-methyl phenylethyl, 2, 4-dichlorobenzyl, or 3,5-dimethoxy 4-methyl benzyl.

When X and Y, or X and $R_3$, or X and $R_4$, or A and B together form an alkylene chain, the rings so formed are preferably piperidine, pyrrolidine, hoxamethylenimine or hexahydroazocine rings. These alkylene chains can be interrupted by a hetero-atom for example, nitrogen, sulphur or oxygen, resulting in an oxazolidine, thiazolidine, morpholine, thiamorpholine, homomorpholine, imidazolidine, isoxazolidine or tetrahydro-m-oxazine rings.

Amongst the compounds of the present invention, there may be mentioned especially:

The ortho-alkoxy- anilides of the general formula

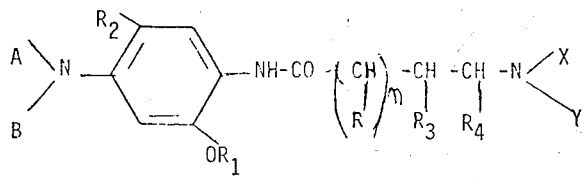

(1)

in which n is zero or an integer from one to three,

R represents a hydrogen atom or a lower alkyl radical, $R_1$ represents a lower alkyl radical, a lower alkenyl radical or a lower phenyl-alkyl radical, $R_2$ represents a lower alkoxy radical or a halogen atom, $R_3$ represents a hydrogen atom or a lower alkyl radical, $R_4$ represents a hydrogen atom or a lower alkyl radical, X and Y, which may be the same or different, each represents a lower alkyl radical or X and Y together with the nitrogen atom to which they are attached form a saturated heterocycle optionally containing one or two other hetero-atoms and having from 3 to 7 ring members, or X and $R_3$ together form an alkylene chain having from 2 to 4 carbon atoms or X and $R_4$ together form an alkylene chain having from 2 to 4 carbon atoms optionally containing one or two hetero-atoms, A and B, which may be the same or different, each represents a hydrogen atom, a lower alkyl radical or an acyl radical derived from an organic carboxylic acid having from 1 to 18 carbon atoms, or A and B are both oxygen atoms or A and B together form an alkylene chain having from 2 to 6 carbon atoms, and more specifically 1-[(N-ethyl pyrrolidin 2-yl) acetylamino] 2-methoxy 4- amino 5-chloro benzene;

1-[(N-methyl-piperid-2-yl)-acetylamino] -2-methoxy-4-amino-5-chloro-benzene;

1-(N-ethyl-piperid-3-yl-carboxamido)-2-methoxy-4-amino-5- chlorobenzene, 1-(β-N,N-diethylamino-propionylamino) -2-methoxy-4-nitro-5-chloro-benzene; and 1-(β-N,N-diethylamino-propionylamino)-2-methoxy-4-amino-5-chlorobenzene.

The compounds of the present application exhibit valuable pharmacological properties. More especially they show a strong inhibitory effect on the gastric secretion. In contrast thereof they do not exhibit any anti-emetic properties, and they do not depress significantly the central nervous system. Because of this, they are useful in human and animal therapy, and especially in gastro-enterology, for the prevention or treatment of digestive disorders and ulcers due to gastric hypersecretion.

In addition thereof 1- [(N-ethyl pyrrolidin-2 yl) acetylamino] 2-methoxy 4- amino 5- chloro benzene exhibits a very potent anti-emetic activity, far superior to that of metoclopramide.

The present invention therefore provides pharmaceutical compositions comprising, as active ingredient, at least one compound of the general formula I in the free form or in the form of a salt, in admixture or conjunction with an inert pharmaceutical excipient.

The compositions are in a form suitable for oral, parenteral, rectal, perlingual or percutaneous administration, as for example, uncoated or coated tablets, injectable suspensions or solutions packaged in ampoules, in multi-dose bottles or in self-injectable syringes, suppositories, sublingual tablets or solutions for percutaneous use.

Their posology may vary depending on the age of the patient, the therapeutic requirements and the method of administration. It may range especially between 20 and 400mg per day and 10 to 100mg per unit dosage.

The present invention also provides a process for the preparation of the compounds of the general formula I which comprises condensing an o-alkoxy-aniline of the general formula

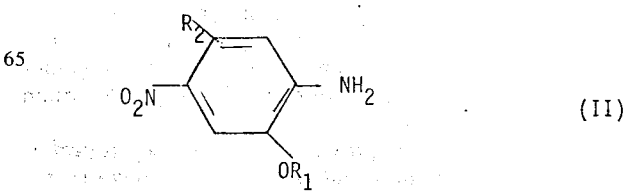

(II)

in which $R_1$ and $R_2$ have the meanings given above, with an amino-alkylcarboxylic acid of the general formula

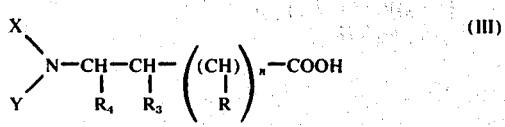

in which R, $R_3$, $R_4$, X, Y and $n$ have the meanings given above, or with a functional derivative thereof to form an anilide of the general formula

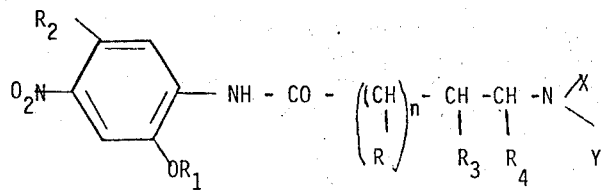

in which R, $R_3$, $R_4$, X, Y and $n$ have the above-specified meanings; optionally when $R_2$ is a halogen, exchanging this radical with a cyano, a lower alkylthio or a trifluoromethoxy radical by means of an alkali metal cyanide, an alkali metal mercaptide or an alkali- metal alcoholate and, optionally reducing the nitro group by means of a metal reducing agent or a mixed hydride to form the corresponding amine of the general formula

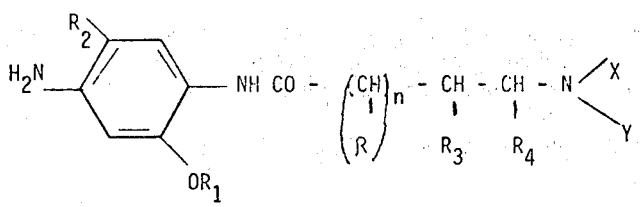

and, if desired, alkylating and/ or acylating the amino group to form a compound in which A and/ or B represents a lower alkyl radical or an acyl radical, or an alkylene chain.

The compounds of the general formula I possess at least one basic group and can be salified by addition of an inorganic or organic acid, for example, hydrochloric acid, sulphuric acid, nitric acid, phosphoric acid, formic acid, butyric acid, benzoic acid, nicotinic acid, tartaric acid, glucose-1-phosphoric acid, embonic acid an ethane-sulphonic acid.

When the amino-alkyl-carboxylic acid portion possesses at least one asymmetric carbon atom, it is possible to resolve the compound of the general formula 1 into its optical isomers by forming a salt with an optically-active inorganic or organic acid. Amongst the acids which are most suitable for such solution, there may be mentioned d- and l-tartaric acids, d- and l-camphoric acids, N, N-dimethyl-d- and-l- tartramic acids and optically-active bis-naphthyl-phosphoric acid.

As the starting material, for the process of the present invention it is also possible to use an amino-alkyl-carboxylic acid of the formula II which has already been resolved. The anilide of the general formula IV produced is thus in an optically-active form. It can also be advantageous to resolve the molecule at the stage of the compound IV by means of the same reagents as those listed above.

According to a preferred method of carrying out the process according to the present invention, a. the functional derivative of the amino-alkyl-carboxylic acid of the formula III is an acid halide, the anhydride, a mixed anhydride or an alkyl, aryl or aralkyl ester;

b. the mixed anhydride is preferably formed in situ with a dehydrating reagent, for example, a dicycloalkyl-carbodiimide, ethoxy-acetylene, a cyanogen halide or carbonyldiimidazole;

c. the condensation is carried out by employing, as the functional derivative of the acid of the general formula III, an acid halide, for example the acid chloride, in the presence of an acid acceptor, for example, an inorganic base, a trialkyl-amine, a pyridyl base, dimethyl-aniline or an excess of the alkoxy-aniline of the general formula II;

d. the condensation is carried out in an inert solvent, for example, a halogenated solvent, a linear or aliphatic ether, an alkane-nitrile, an aromatic hydrocarbon, for example toluene or xylene, a tertiary alcohol, for example tertiary butanol or tertiary amyl alcohol, or an aprotic polar solvent for example dimethylformamide or hexaphosphorotriamide;

e. the reduction hydrogenation the compound of the formula IV is effected by hydrogeneation in the presence of a catalyst of the platinum group, for example platinum, palladium or rhodium, in the presence of Raney nickel or by means of a metal reducing agent such as iron, tin or zinc in an acid medium;

f. the alkylation of the compounds of the general formula II is effected either by reaction with an aldehyde or a ketone in the presence of formic acid by the Leuckart reaction, or by formation of a Schiff's base followed by reduction to the amine by the action of an alkali metal borohydride;

g. the acylation of the compounds of the formula V is effected by means of an acid halide in the presence of a pyridyl base, for example, pyridine, collidine or 4-dimethyl-amino pyridine.

The starting materials of the general formula III are described in the literature. They can be prepared, especially when they are cyclic, by catalytic hydrogenation of the corresponding aromatic hetero-acid followed by alkylation at the nitrogen atom.

from the group comprising an arylsulphonyloxy radical, a lower alkyl sulphonyloxy radical, a halogen and a silyloxy radical. or a functional derivative thereof, to produce a substituted anilide of the formula VII

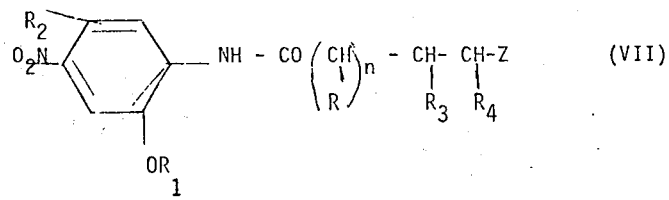

The 2-amino-4-halo-5-nitro-1-alkyl or -alkenyl or -aralkylphenols of the general formula II can be prepared in accordance with the process described in Belgian Patent No. 688,790, by reacting an alkali metal alcoholate with a 2- acylamino -4- halo-5-nitro-alkoxyphenol, 2-acylamino-4-alkoxy-5- nitro- alkoxyphenol can be prepared, hydrolysis of which in an acid medium leads to a 2-amino-4- alkoxy-5- nitro- alkoxyphenol of the general formula II in which $R_2$ represents a lower alkoxy radical.

The invention provides another process for preparing the compounds of general formula 1 in which the substituents $R_1$, $R_2$, R, $R_3$, $R_4$, Z and $n$ are defined as above-specified
and condensing the latter with an amino derivative of the formula VIII

in which X and Y, which may be the same or different, each represents a lower alkyl radical or X and Y to-

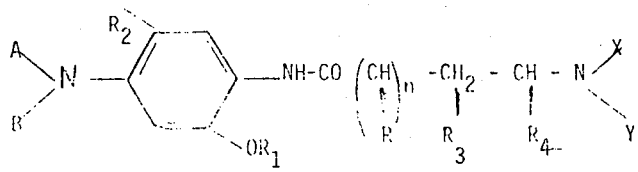

in which X and Y are each a lower alkyl or together form a lower alkylene chain which may be interrupted by one or two heteroatoms selected from the group consisting of nitrogen, oxygen and sulphur, and the other substituents are defined as above-specified which consists in condensing an o. alkoxy aniline of the general formula II

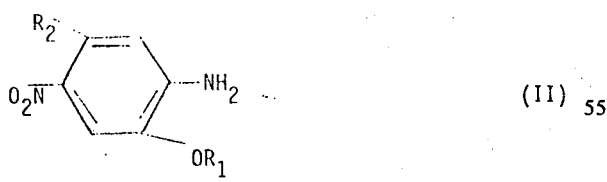

in which $R_1$ and $R_2$ have the meanings given above, with an ω-substituted alkyl carboxylic acid of the formula VI

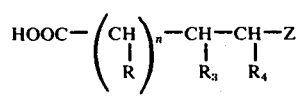

in which
  R is a hydrogen or a lower alkyl radical,
  $n$ is zero or an integer from 1 to 3,
  $R_3$ represents a hydrogen or a lower alkyl radical,
  $R_4$ represents a hydrogen or a lower alkyl radical, and
  Z is a substituent which may be easily split, selected gether with the nitrogen atom to which they are attached, form a saturated heterocycle optionnally containing one or two heteroatoms and having from 3 to 7 ring atoms,
and recovering a compound of general formula IX

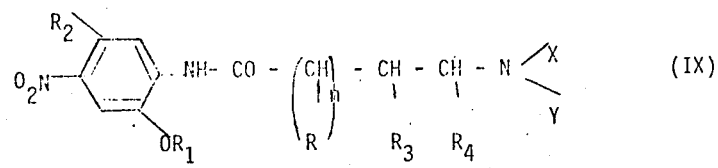

in which $R_1$, $R_2$, $R_3$, $R_4$ and $n$ are defined as previously given and X and Y have the here above specified meanings,
which may be further be reduced into the corresponding amino compound of the formula

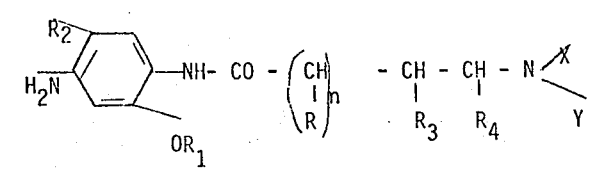

in which the substituents $R_1$, $R_2$, R, $R_3$, $R_4$, X, Y and $n$ are defined as above-specified,
by means of a metal reducing agent or a metal mixed hydride which may be further, when desired, salified by addition of a mineral or organic acid or resolved when the aminoacyl side-chain includes at least one asymetric carbon atom, acylated and / or alkylated.

Preferably the substituent Z in the compounds of general formula VI is a halogen such as a fluorine or chlorine atom, in the presence or absence of an alkali-metal iodide. It may also be a methane sulphonyloxy radical, a p. toluenesulphonyloxy radical or a naphlylsulphonyloxy radical. The reaction between a compound of general formula VI and the substituted aniline of general formula II is performed in an inert organic solvent such as halogenated alkane, an alkyl cyanide such as acetonitrile, a nitroalkane such as nitromethane, a carbonyl-substituted alkane such as acetone, methyl ethylketone or methylisobutylketone, a linear or cyclic ether such as ethyl or isopropyyl ether or tetrahydrofuran; a base such as pyridine, dimethylaniline or 4- dimethylaminopyridine; a polar aprotic solvent such as dimethyl formamide, dimethyl acetamide, hexamethyl phosphoramide, divinyl sulfone or dimethylsulphoxide.

The compound of general formula IV may be the free acid or a salt thereof or preferably a functional derivative thereof such a halide, a lower alkyl or an aryl ester, the anhydride or a mixed anhydride. The halide may be formed "in situ" by contacting the free acid with an halogenating reagent such as thionyl chloride in a polar solvent such as hexamethyl phosphoramide.

The invention also extends to the intermediate compounds of general formula VII and namely to 1-(β-chloropropionylamino) 2- methoxy 4- nitro 5- chlorobenzene. The following Examples illustrate the invention.

EXAMPLE 1

1- (N,N-diethylamino-propionyl) - amino -2-methoxy-4-nitro-5- chlorobenzene and its hydrochloride 3,6 g of N, N- diethylamino-propionic acid hydrochloride are dissolved in 90 ml of hexamethylphosphoramide. The solution is cooled to +5 to 10° C and 1.5 ml of thionyl chloride are added gradually. The mixture is stirred at +5° for one hour. 4g of 2-amino-4-chloro-5-nitroanisole are then added in small portions and stirring is continued overnight at room temperature.

The precipitate of 1-(N,N-diethylaminopropionylamino)-2-methoxy -4-nitro-5-chloro-benzene hydrochloride which has formed is then filtered off, washed with hexamethylphosphoramide and then with ether and dried in vacuo at 60°.

After recrystallisation from isopropanol, 5,7 g of a product which melts at 215°–220° (with sublimation) are collected, corresponding to a yield of 78%.

The IR spectrum indicated the presence of a secondary amide group (bands at 1,700 cm$^{-1}$ and at 1,530 cm$^{-1}$) and of a nitro group (bands at 1,510cm$^{-1}$ and 1,330 cm$^{-1}$).

| Analysis | C$_{14}$H$_{20}$ClN$_3$O$_4$ . HCl = 366.246 | | | |
|---|---|---|---|---|
| | C % | H % | N % | CL % |
| Calculated | 45.92 | 5.78 | 11.47 | 19.37 |
| Found | 45.85 | 5.94 | 11.33 | 19.02 |

1-(N,N-Diethylaminopropionylamino)-2- methoxy-4-nitro-5- chlorobenzene hydrochloride dissolved in water is converted to the base by adding sodium hydroxide solution until the mixture is markedly alkaline.

In the same manner starting from 2- amino-4- chloro -5- nitro anisole and (N-methyl piperidin -2yl) acetic acid 1 [(N-methylpiperidin -2yl) acetylamino] 2- methoxy 4- nitro 5 chloro benzene hydrochloride is obtained.

EXAMPLE II

1-(N,N-diethylamino-propionylamino) -2-methoxy -4-amino-5-chloro-benzene and its hydrochloride 3.6 g of 1-(N,N-diethylamino-propionylamino) -2-methoxy-4- nitro -5-chloro-benzene hydrochloric produced in Example I are dissolved in 120 ml of methanol. 0.5 g of Raney nickel is added and reaction vessel is purged with nitrogen. Hydrogenation is then carried out at room temperature and under normal pressure. After the theoretical volume of hydrogen has been absorbed, the catalyst is removed and washed with methanol. The combined methanol solutions are evaporated to dryness in vacuo.

The residue is taken up in 30 ml of hot methanol from which it crystallises on cooling. The crystals are isolated, washed with cold methanol and dried in vacuo, 2g of 1-(N,N-diethylamino-propionylamino) -2-methoxy-4-amino-5-chlorobenzene hydrochloride are thus obtained, corresponding to a yield of 60%. The pure product melts at 218°–220°.

The IR spectrum indicates the presence of a primary amine group (bands at 3,460 cm$^{-1}$ and 3,360 cm$^{-1}$), the absence of a nitro group and the presence of a secondary amide group (band 1-1,680cm$^{-1}$ and band II at 1,520 cm$^{-1}$).

| Analysis: | C$_{14}$ H$_{22}$ ClN$_3$ O$_2$ . HCL = 336.26 | | | |
|---|---|---|---|---|
| | C % | H % | N % | Cl % |
| Calculated | 50.01 | 6.90 | 12.50 | 21.09 |
| Found | 49.97 | 7.06 | 12.33 | 20.82 |
| | 50.23 | 7.10 | 12.29 | 20.94 |

1-(N,N-diethylamino-propionylamino)-2-methoxy-4-amino-5- chlorobenzene is produced by rendering alkaline a solution of the hydrochloride.

In the same manner 1-[(N-methylpiperidin-2yl) acetylamino] 2-methoxy 4- nitro 5- chloro benzene hydrochloride is reduced to 1[N-methylpiperidin -2yl acetylamino] -2-methoxy 4- amino 5- chlorobenzene (hydrochloride). It melts at 135°–142° after recrystallization from a mixture of acetonitrile and ethanol.

It is freely soluble in water.

EXAMPLE III

1-[(N-ethyl-pyrrolidin-2-yl)-acetylamino]-2-methoxy-4-nitro-5-chlorobenzene

Following the procedure described in Example I, and starting from N-ethyl-pyrrolidin 2-yl acetic acid hydrochloride and 2- amino-4- chloro-5-nitro-anisole, there is obtained 1- [(N- ethyl-pyrrolidin-2-yl) acetylamino] -2-methoxy -4- nitro-5- chloro-benzene(hydrochloride)

| Analysis: | C$_{15}$ H$_{22}$ CL N$_3$ O$_2$, HCL = 348.27 | | |
|---|---|---|---|
| | C % | H % | N % |
| Calculated | 51.74 | 6.66 | 12.07 |
| Found | 51.25 | 6.79 | 11.77 |

Melting point: 211–213° C
IR Spectrum: absorption of the amide carbonyl group at 1670 cm$^{-1}$
absorption of the amide imino group (NH) at 1540 cm$^{-1}$ It is also possible to produce 1-[(N-ethyl-pyrrolidin-2-yl)-acetylamino]-2-methoxy-4- nitro-5-chloro-benzene by condensing 2- amino-4-chloro-5-nitro-anisole with ethyl (N-ethyl-pyrrolidin-2-yl)- acetate in dimethylsulphoxide in the presence of sodamide. The yield is 85%.

Ethyl (N-ethyl-pyrrolidin-2-yl)-acetate is produced by the method described by F.P. Doyle, J, Chem. Soc., 1958, 4458.

1-[(N-Ethyl-pyrrolidin-2-yl)-acetylamino]-2-methoxy-4-amino-5-chloro-benzene is produced by reducing 1-[(N-ethyl-pyrrolidin-2-yl)-acetylamino]-2-methoxy-4-nitro-5-chloro-benzene with potassium borohydride in the presence of a trace of palladium chloride.

EXAMPLE IV

1-[(N-ethyl-piperid-3-yl)-carboxamido]-2-methoxy-4-nitro-5-chloro-benzene 1.85 g of ethyl 1-ethyl-piperid-3-yl-carboxylate, 2.02g of 2- amino-4- chloro-5- nitro-anisole and 0.5 g of a dispersion of sodium hydride in vaseline oil are dissolved in 50 ml of dimethylsulphoxide. The reaction mixture is stirred overnight at room temperature and is then poured into a mixture of ice and water. The crystalline precipitate is isolated, washed with water, drained then rinsed with a few ml of pentane and dried in vacuo.

2.3 gg of 1-[(N-ethyl-piperid-3-yl)-carboxamido]-2-methoxy-4-nitro-5-chloro-benzene are thus isolated and are recrystallised from isopropyl ether for analysis.

The latter is reduced to 1-[(N-ethyl-piperid-3-yl)-carboxamido]-2-methoxy -4-amino-5-chloro-benzene in accordance with the procedure described in Example 2.

1-[(N-Ethyl-piperid-3-yl)carboxamido]-2-methoxy-4-amino-5-chlorobenzene is converted into its hydrochloride by passing a current of hydrogen chloride into an ethereal solution of the free base.

| Analysis: | $C_{15}H_{22}Cl\,N_3O_2 \cdot HCL = 348.27$ | | | |
|---|---|---|---|---|
| | C % | H % | N % | CL % |
| Calculated | 51.74 | 6.66 | 12.07 | 20.36 |
| Found | 51.14 | 6.18 | 11.87 | 20.27 |
| I.R. Spectrum: absorption of the amide carbonyl group at 1660 cm$^{-1}$ absorption of the amide imino group at 1530 cm$^{-1}$ | | | | |

EXAMPLE V 1-(N,N-diethylamino-propionylamino)-2-methoxy-4-dimethylamino-5-chlorobenzene 0.91 g of 1-(N,N-diethylamino-propionylamino)-2-methoxy-4-amino-5-chloro-benzene is introduced with stirring into 10 ml of 40% formaldehyde and 2 g of zinc powder and 10 ml of acetic acid are then added. Stirring is then continued for three and a half hours at a temperature of about 20°. The precipitate is then isolated, drained and washed with acetic acid and then with water; the filtrates are combined and are rendered alkaline to pH 10 by adding sodium hydroxide solution and extraction is carried out with methylene chloride.

The organic solution is isolated, washed with water, dried and then distilled in vacuo. The dry residue, taken up in isopropyl ether, crystallises. 0.69 g of 1-($\beta$-N,N-diethylamino-propionylamino)-2-methoxy-4-dimethylamino-5-chloro-benzene is obtained.

EXAMPLE VI

1-[($\beta$-morpholinylpropionylamino)] 2- methoxy 4- amino -5- chlorobenzene

Step A 1-($\beta$chloro propionylamino) 2- methoxy 4- nitro 5-chlorobenzene 17.2 g of 2- methoxy 4- nitro 5- chloroaniline dissolved in 150 ml benzene are added with 11.1g of $\beta$chloropropionyl chloride dissolved in 40 ml benzene and 2 ml pyridine. The reaction mixture is kept under stirring at room temperature for two hours then diluted with 250 ml water. The benzenic phase is separated while the aqueous phase is extracted twice with benzene. The benzenic solutions are united, washed with 2N hydrochloric acid then with water dried on sodium sulphate, filtered and evaporated to dryness. The dry residue is recristallised from isopropyl ether and 21.1g of 1($\beta$chloropropionylamino) 2- methoxy 4- nitro 5-chlorobenzene are recovered (yield 40–50%). It melts at 101°–110° (dec)

Step B

1($\beta$-morpholinylpropionylamino) 2- methoxy 4- nitro 5- chloro benzene 10.6g of 1($\beta$chloropropionylamino) 2-methoxy 4-nitro 5- chlorobenzene obtained at step A are dissolved in 50 ml tetrahydrofuran. To this solution 1.8g of potassium carbonate are added, then dropwise 3.85 g of morpholine.

The mixture is heated to reflux for 4 hours then let to revert to room temperature. After one hour standing the precipitate is filtered then rinced with few ml of tetrahydrofuran and the organic solutions are united. The solvent is distilled off until half volume under reduced pressure and an equal volume of cyclohexane is added. Crystallisation of the morpholinyl derivative is initiated by scratching then the flask is placed in the refrigerator for a night. The crystals are thereafter separated by filtration, rinced with cyclohexane and dried in an oven. 11.62 g of I-( $\beta$-morpholinylpropionylamino) 2-methoxy 4- nitro 5-chlorobenzene are thus recovered (yield 77%). It melts after recrystallisation (yield 60%) at 161°–163° C.

Step C 1-($\beta$-morpholinylpropionylamino) 2- methoxy 4- amino 5- chlorobenzene Using the same procedure as in example II the 4-amino derivative is obtained with a yield of 81%. After crystallisation from Methyl Cellosolve it melts at 192°–196°.

By dissolving it in the stoechio metric amount of N hydrochloric acid and distilling off the water the hydrochloride of 1($\beta$-morpholinylpropionylamino) 2- methoxy 4- amino 5- chlorobenzene is recovered.

| Analysis | $C_{14}H_{20}CL\,N_3O_3 = 313, 78$ | | | |
|---|---|---|---|---|
| | C | H | N | CL % |
| Calculated | 53.60 | 6.42 | 13.39 | 11.30 |
| Found | 53.55 | 6.40 | 13.05 | 11.18 |

Using the procedure of step B but replacing the morpholine with piperidine and of step C, 1-($\beta$piperidinopropionylamino) 2- methoxy 4-amino 5- chlorobenzene is obtained.

Using the procedure of step B but replacing the morpholine with disopropylamine and of step C, 1-($\beta$diisopropylaminopropionylamino) 2-methoxy 4- amino 5- chlorobenzene is obtained.

EXAMPLE VII 1 (N-ethyl pyrrolidin -2yl) acetylamino 2- methoxy 4-nitro 5- cyanobenzene 7g of 1 [(N- ethylpyrrolidin -2yl) acetylamino] 2- methoxy 4- nitro 5-chlorobenzene hydrochloride obtained according to example III are dissolved in 60 ml dimethyl sulfoxide and 4g silver cyanide are added. The mixture is heated to reflux for five hours and let thereafter to return to room temperature. The precipitate is filtered and washed with few ml of dimethylsulfoxide. The filtrate is concentrated under reduced pressure to 20ml then diluted with 200ml water. The thus formed suspension is kept under stirring for one hour in a cool place then filtered. The precipitate is washed with water then dried.

For analysis purposes 1- [(N-ethylpyrrolidin-2yl) acetylamino] 2- methoxy 4- nitro 5- cyanobenzene is recrystallised from hot isopropylether 4.98 g of pure compound are thus obtained.

In the same manner replacing silver cyanide with sodium ethylmercaptide 1-[(N-ethylpyrrolidin 2-yl) acetylamino] 2- methoxy 4- nitro 5-ethylthio benzene is obtained.

In the same manner replacing silver cyanide with potassium trifluoromethoxide, 1-[(N-ethylpyrrolidin -2yl) acetylamino] 2- methoxy 4- nitro 5- trifluoromethoxy benzene is obtained.

These nitro derivatives may be further reduced into the corresponding 1-[(N-ethylpyrrolidin 2-yl) acetylamino]2- methoxy 4-amino 5-$R_2$ benzene using the procedure of example II with a yield of about 80%.

EXAMPLE VIII

Pharmaceutical study of the compounds of the formula I

A. acute toxicity and general activity on behaviour

On the mice: the first active dosis is 25 mg/kg IP. It induces a decrease in the exploratory activity and a decrease in the respiratory rythm.

Higher dosages induce a decrease in the motility then a decrease in the muscular tone, analgesia and ataxia. At very high dosages convulsions are caused with handling of the mice. The avery letal dosis (LD50) have been calculated ranging from 50 to 250mg/kg introperitoneally, generally between 100 and 175mg/kg.

On the rats: the motility and the muscular tone are only depressed for a short period of time.

On the dogs: the respiratory rythm is increased in connexion of a state of excitation and increase of motility.

The compounds are thus deprived of any neuroleptic action. It appears to be slightly sedative and myorelaxant.

B. effect on gastric evacuation

The stimulating effect on gastric evacuation was determined by the method of Brodie ( Fed. Proc. 25 (1965) 714).

In this method the speed at which pellets of Amberlite of regular shape and previously introduced by tubing into the stomach, are expelled, is determined on groups of rats fasted for 12 hours.

The compounds to be tested are administered by subcutaneous way and the avery active dosis which is the minimal dosis which increases of 50% the gastric evacuation has been found from 2.75mg/Kg to 30mg/Kg.

In comparison thereof 1-[N-ethylpyrrolidin -2yl] acetyl 2-methoxy 5- sulphamoyl aniline selected as a reference compound had a $ED_{50}$ of 44 mg/kg.

C. effect on gastric secretions

The inhibitory effect on gastric secretions was determined on groups of rats using the method described by H. G. Shay and coll. The gastric secretions are collected 4 hours after ligature of the pylorus and the total acidity thereof is determined by means of an Autopipetting system Radiometer (titration by 0.1 N NaOH until pH= 8.45)

The tested doses administered intraperitoneally ranged from 10 to 100mg/kg. The $ED_{50}$ is from about 20mg/kg to about 40mg/kg. In similar experimental conditions at a dose of 30mg/kg, the reference product is without effect.

Similarly Metoclopramide is devoid of any effect on the gastric secretions.

EXAMPLE IX

Tablets containing 50 mg of [(N-methylpiperid -2-yl) acetylamino] -2- methoxy -4- amino 5- chloro benzene per unit dosage:

| Active ingredient | 500 g |
|---|---|
| Starch | 225 g |
| Ethyl cellulose | 5 g |
| Calcium carbonate | 200 g |
| Magnesium Stearate | 25 g |
| Talc | 25 g |
| Silica | 20 g |
| for 10,000 tablets weighing each about 100mg. | |

Tablets containing 30mg of 1- [(N-ethylpyrrolidin -2yl) acetylamino] 2- methoxy 4- amino 5: chlorobenzene per unit dosage.

| Active ingredient | 300 g |
|---|---|
| Talc | 1200g |
| Ethyl Cellulose | 50 g |
| Magnesium phosphate | 430 g |
| Methyl cellulose (sold under the Trade Name of Methocel) | 25 g |
| for 10,000 tablets weighing about 200mg. | |

What we claim is:
1. A compound of the formula

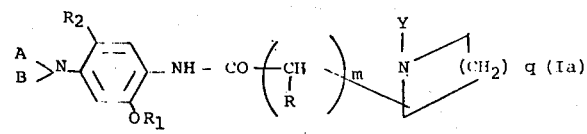

wherein:
 $m$ is O or an integer of 1 to 5;
 $q$ is 3;
 R is hydrogen or lower alkyl of 1 to 6 carbon atoms in the chain;
 $R_1$ is lower alkyl of 1 to 6 carbon atoms, lower alkenyl of 2 to 6 carbon atoms, or phenyl lower alkyl of 1 to 4 carbon atoms in the side chain;
 $R_2$ is halo or lower alkoxy of 1 to 6 carbon atoms;
 Y is lower alkyl of 1–6 carbon atoms
 A and B which may be the same or different, each represents a hydrogen atom, a lower alkyl radical or an acyl radical derived from an organic carboxylic acid of from 1 to 18 carbon atoms.

2. 1- [(N-methyl-piperid -2-yl)-acetylamino]-2- methoxy -4-amino -5-chloro benzene being a compound of claim 1.

3. 1-(N- ethyl- piperid-3-yl-carboxamido)-2- methoxy -4- amino-5-chloro benzene being a compound of claim 1.

4. A pharmaceutical composition for treating or preventing gastric ulcers due to gastric hypersecretion and/or delay in gastric evacuation comprising, as active ingredient, an effective amount of at least one compound of claim 1 in the free form or in the form of a salt, in admixture or conjunction with an inert pharmaceutical excipient.

5. A pharmaceutical composition according to claim 4 wherein the amount of active ingredient ranges from 10 to 100mg per unit dosage.

6. A method for treating or preventing gastric ulcers due to gastric hypersecretion and/or delay in gastric evacuation which consists in administering to warm-blooded animals suffering or disposed to suffer from said ailments a gastric secretion inhibitory effective amount of a compound of claim 1.

7. The method of claim 6 wherein the effective amount ranges from 0.5mg/kg to 6.6 mg/kg.

* * * * *